United States Patent [19]
Pernisz

[11] Patent Number: 5,403,748
[45] Date of Patent: Apr. 4, 1995

[54] DETECTION OF REACTIVE GASES

[75] Inventor: Udo C. Pernisz, Midland, Mich.

[73] Assignee: Dow Corning Corporation, Midland, Mich.

[21] Appl. No.: 131,278

[22] Filed: Oct. 4, 1993

[51] Int. Cl.⁶ .............................................. G01N 33/00
[52] U.S. Cl. .................................. 436/113; 436/116; 436/136; 436/149; 436/151
[58] Field of Search ............... 456/113, 116, 136, 149, 456/151

[56] References Cited

U.S. PATENT DOCUMENTS

| | | | |
|---|---|---|---|
| 3,149,398 | 9/1964 | Sprague | 29/25 |
| 3,271,591 | 9/1966 | Ovshinsky | 307/88 |
| 3,953,375 | 4/1976 | Nagano | 252/520 |
| 4,052,340 | 10/1977 | Einthoven | 252/518 |
| 4,507,394 | 3/1985 | Mase | 501/94 |
| 4,756,977 | 7/1988 | Haluska | 428/704 |
| 5,151,384 | 9/1992 | Williams | 437/170 |
| 5,283,545 | 2/1994 | Pernisz et al. | 338/308 |
| 5,293,335 | 3/1994 | Pernisz et al. | |
| 5,312,684 | 5/1994 | Michael et al. | 428/336 |

FOREIGN PATENT DOCUMENTS 512717 11/1992 European Pat. Off. .
WO9000826 1/1990 WIPO .

OTHER PUBLICATIONS

Bullot et al., Physica Status Solidi, (a) 71, K1–K4 (1982). "Threshold Switching in V₂O₅ Layers Deposited from Gels".
Ansari et al., Journal of Physics, 20, (1987), pp. 1063–1066. "Pre- and Post-threshold Coduction Mechanisms in Thermally Grown . . .".
Ramesham et al., NASA Tech Briefs, Dec. 1989, p. 28.
Morgan et al., Thin Solid Films, 20, (1974), pp. S7–S9. "Electroforming and Dielectric Brakedown in Thin Aluminum Oxide Films".
Boelle et al., Applied Surface Science, 46, (1990) pp. 200–205.
Klein, Journal of Applied Physics, vol. 40, No. 7, Jun. (1969), pp. 2728–2740.
Morgan et al., Thin Solid Films, 15 (1973) pp. 123–131.
Simmons, Handbook of Thin Film Technology, Chapter 14 (1970) pp. 14–38 to 14–43.
Al-Ismail et al., Journal of Material Science, 20 (1985) pp. 2186–2192.

*Primary Examiner*—Donald E. Czaja
*Assistant Examiner*—Milton I. Cano
*Attorney, Agent, or Firm*—James L. DeCesare

[57] ABSTRACT

A method of detecting the presence or measuring the concentration, of a reactive gas in an inert ambient gas by (i) placing a silicon dioxide film derived from the oxidation of a hydrogen silsesquioxane resin in the inert ambient gas; (ii) passing the inert ambient gas over the film; (iii) monitoring a change in the current flow through the film at a voltage below and above a threshold voltage, as an indication of the presence in the inert ambient gas of a reactive gas; and (iv) determining the threshold voltage of the film as a measure of the concentration of the reactive gas in the inert ambient gas. The silicon dioxide film is characterized by a current-voltage curve which includes both linear and non-linear regions.

16 Claims, 5 Drawing Sheets

DETECTION OF REACTIVE GASES

BACKGROUND OF THE INVENTION

This invention is directed to threshold switching devices which exhibit negative differential resistance (NDR), and to certain ceramic threshold switching devices which are useful in the detection of reactive gases in a fluid stream.

Devices which exhibit threshold switching, and metal oxide devices which exhibit threshold switching with negative differential resistance (NDR), are known in the art. The switching and negative differential resistance (NDR) characteristics of silicon oxide films have also been described in the literature.

The use of thin film silica coatings derived from hydrogen silsesquioxane resin to provide protection and electrical insulation is not new, but the use of those coatings to form switching devices which are useful in the detection of reactive and inert gases is believed to be novel.

Coatings and switching devices formed by depositing a thin hydrogen silsesquioxane derived silicon dioxide film between at least two electrodes and applying a voltage above a threshold voltage across the electrodes, are described in detail in a prior copending patent application U.S. Ser. No. 07/694721 filed May 2, 1991 now U.S. Pat. No. 5,312,648, and entitled "Threshold Switching Devices".

Such coatings and switching devices have also been described in another copending application assigned to the same assignee as the present application, U.S. Ser. No. 07/915572, filed Jul. 20, 1992 now U.S. Pat. No. 5,283,545, entitled "Variable Resistors".

The present invention involves these coatings and switching devices and their utility in gas detection applications.

It has been discovered that switching devices with desirable features can be formed by depositing a thin hydrogen silsesquioxane derived silicon dioxide film between at least two electrodes, and applying a voltage above a threshold voltage across the electrodes. These ceramic devices are useful in the sensing of reactive gases present in a fluid stream.

SUMMARY OF THE INVENTION

The present invention relates to a threshold switching device having negative differential resistance (NDR) formed by depositing a non-dense silicon dioxide film derived from hydrogen silsesquioxane resin between at least two electrodes. A voltage above a certain threshold voltage is then applied across the electrodes to complete the formation of the device (electro-forming).

A device formed in this manner is characterized in that (i) the conductive state of the device exhibits a region of stable voltage-controlled negative differential resistance, (ii) the conductive state can be converted to a resistive state by decreasing the applied voltage from a sufficiently high value to a value below a threshold voltage at a sufficiently high rate, (iii) the device can be converted from a resistive state to a conductive state by the application of a voltage above the threshold voltage, (iv) the presence of a reactive gas in the inert ambient gas or fluid stream to which the device is exposed induces a transition from the conductive state of the device to its resistive state for an applied voltage above a reaction barrier voltage, and (v) the value of the threshold voltage at which transition (iii) occurs is a monotonic function of the concentration of reactive gas in the inert ambient gas or fluid stream to which the device is exposed.

Because of these unique characteristics, the devices of the present invention are capable of functioning as gas sensitive films for detecting a change in a gaseous ambient from one type of gas to another type of gas.

Specifically, these device characteristics are utilized in a method of detecting the presence of a reactive gas in a fluid stream of an inert ambient gas by (i) placing a device according to the present invention in the fluid stream; (ii) exposing at least part of the thin film and an electrode to the fluid stream; and (iii) monitoring the current flow through the film at a constant voltage. A rapid drop in the current is an indication of the presence in the fluid stream of a reactive gas.

Two modes of operation are possible depending on the value of the applied voltage. For a voltage above $V_{eb}$, the reaction barrier voltage, but below $V_{th}$, the threshold voltage, the drop in current is permanent (until the device is sensitized again) and records the event of the increase in the reactive gas concentration in a "sentinel mode" of operation. For a voltage above the $V_{th}$ but below $V_{mn}$, the current minimum voltage, the drop in current is reversible after the reactive gas is removed from the fluid stream flowing over the device. The current increases again after the reactive gas is desorbed from the device surface and purged out. Changes in the composition of the fluid stream are continually followed in a "monitor mode" of operation.

Another feature characteristic of the method according to the present invention involves a procedure in which the device is utilized in a method of determining the concentration of a reactive gas in a fluid stream by (i) placing a device according to the present invention in a fluid stream; (ii) exposing at least part of the thin film and an electrode to the fluid stream; and (iii) determining the threshold voltage of the device by switching the device repeatedly between its conductive (ON) and its resistive state (OFF), and observing the voltage at which the transition from the OFF state to the ON state occurs. This threshold voltage is a monotonic function of the concentration of the reactive gas in the fluid stream.

Additional features characteristic of both methods of utilizing the device according to the present invention as a gas sensor involve procedural steps of preparing, electro-forming, and sensitizing the device in an inert atmosphere prior to placing it into the fluid stream. The device is initially placed into a purging stream of inert gas such as nitrogen to desorb reactive species such as oxygen front the surface of the device. Then the device is sensitized to the presence of a reactive gas in the inert atmosphere by temporarily applying a voltage in excess of the threshold voltage $V_{th}$ (but below the current minimum voltage $V_{mn}$) to the device thus electro-forming it. This operation leaves the device in the conductive (ON) state. The device is then exposed to the gas or fluid stream in which it to operate as a sensor for the reactive gas.

The determination of the threshold voltage consists of (i) increasing the voltage applied to the device to or above the current minimum voltage $V_{mn}$ and from there reducing the voltage at a sufficiently rapid rate to a value below the reaction barrier voltage $V_{eb}$, or to zero, switching the device to its resistive (OFF) state; subsequently (ii) slowly ramping the applied voltage up while measuring the device current to detect the rapid increase in current associated with the device switching to its conductive (ON) state; and finally (iii) noting the voltage at which this transition occurs as the threshold voltage.

During or following these steps, the device is subjected to the fluid stream and, depending on the desired mode of operation, to an applied voltage at which the device current is measured. The foregoing sequence of steps is then repeated.

The reactive gas can be a gas such as oxygen, ammonia, and nitrous oxide, whereas the inert ambient gas and the inert atmosphere are gases such as nitrogen, argon, carbon dioxide, and helium, While the use of ceramic materials as sensor elements for the detection of oxygen gas have been described in the patent literature, representative of which is U.S. Pat. No. 4,507,394 issued Mar. 26, 1985, such sensors are neither manufactured of the same or equivalent materials as the present invention, nor do the prior art sensors exhibit the unique characteristics possessed by the films of the present invention.

These and other features, objects, and advantages, of the present invention will become more apparent from a consideration of the detailed description of the invention.

BRIEF DESCRIPTION OF THE DRAWINGS

FIG. 1 shows the device in its simplest form.

In FIG. 10, the abbreviations used are: ECRB for the electrochemical reaction barrier at voltage $V_{eb}$; THR for the threshold voltage for OFF-ON transition at voltage $V_{th}$; BS-SS for bistable single shot sentinel operating at $V_1 < V_{th}$; and MS-DR for monostable delayed recovery at $V_2 > V_{th}$. $V_{mn}$ designates the voltage above which the device turns OFF as the current reaches its minimum.

DETAILED DESCRIPTION OF THE INVENTION

The present invention is based on the discovery that thin films of silicon dioxide derived from hydrogen silsesquioxane resin exhibit novel threshold switching and negative differential resistance (NDR), as well as stable conductive and resistive states between which transitions can be induced dependent on the gas ambient to which the device is exposed.

Figure 1:
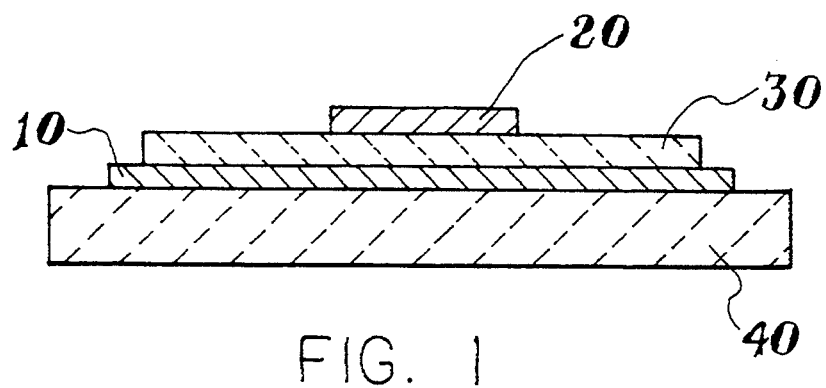
FIG. 1 is pictorial representation and a side view in cross section of a sandwich device according to the present invention.

FIG. 1 shows a threshold switching device of this invention wherein electrodes 10 and 20 are separated by a thin film 30. Although FIG. 1 exemplifies a sandwich electrode configuration including a glass substrate 40, this arrangement is not critical and any configuration may be used. For example, arrangements such as coplanar transplanar, crossed grid arrays, and two-dimensional circular dot patterns may be used.

The electrodes 10 and 20 may be any shape, and can be made of electrically conductive or semiconductive materials such as gold, silver, aluminum, platinum, copper, gallium arsenide, chromium, and silicon. Likewise, the electrodes can be in any form such as a wire or a conventional lead, provided they have at least enough device area to enable current flow. Particularly preferred are gold electrodes.

Contact between the electrodes 10 and 20 and the thin film 30 can be established by techniques known in the art. The electrodes may be formed on the thin film by evaporating or sputtering an appropriate electrode material in vacuum. Alternatively, the thin film 30 may be deposited directly onto preformed electrodes to create a contact, or the preformed electrodes may be adhered to the thin film by conventional techniques.

The thin film 30 constitutes silicon dioxide derived from hydrogen silsesquioxane resin, and these films may be of any thickness. Films in the range of 50–5000 nanometer are preferred, while films in the range of 100–600 nanometer are especially preferred. Such thin films 30 may be formed by coating a substrate with a solution of hydrogen silsesquioxane resin in a solvent, evaporating the solvent to form a preceramic coating, and converting the preceramic coating to a thin film by an oxidizing heat treatment.

The thin film 30 is formed with the electrodes 10 and 20 arranged such that a voltage can be applied across the thin film. A device prepared in this manner initially exhibits an undefined, non-specific resistance. Some devices may exhibit resistance values as low as one ohm while others exhibit values above ten megohm. Those devices with low resistance often have shorts between the electrodes due to pin holes and other flaws. If present, these shorts may be "blown out" by applying a sufficiently high voltage of about 10 volt or higher from a impedance voltage source to vaporize the electrode around the short.

A voltage is then slowly applied across the film of the device and increased until a threshold voltage is reached, at which point the resistance of the device will suddenly fall. Upon application of such a voltage, the device is completely formed and will remain in a low resistance ON state until switched back to OFF again as described below.

To obtain lower threshold voltages and more reproducible results, the device of the invention may be placed in a non-oxidizing environment. Suitable environments include nitrogen, argon, helium, and carbon dioxide. Alternatively, however, establishing a vacuum or encapsulating the device can also provide the deskrad non-oxidizing environment.

The following describes the characteristics of a typical device formed in the above manner, and the procedures to switch the device from its ON state to an OFF state and back again. A typical device includes a silica thin film 30 with a thickness of about 200 nanometer and a device area of about 0.1 $cm^2$ or less. A voltage is applied across the electrodes 10 and 20, and the current through the device and the voltage across the device are measured. The current, measured in ampere (A) is converted to current density j and reported as $A/cm^2$. The results are plotted in a jV diagram of current density versus voltage.

Figure 3:
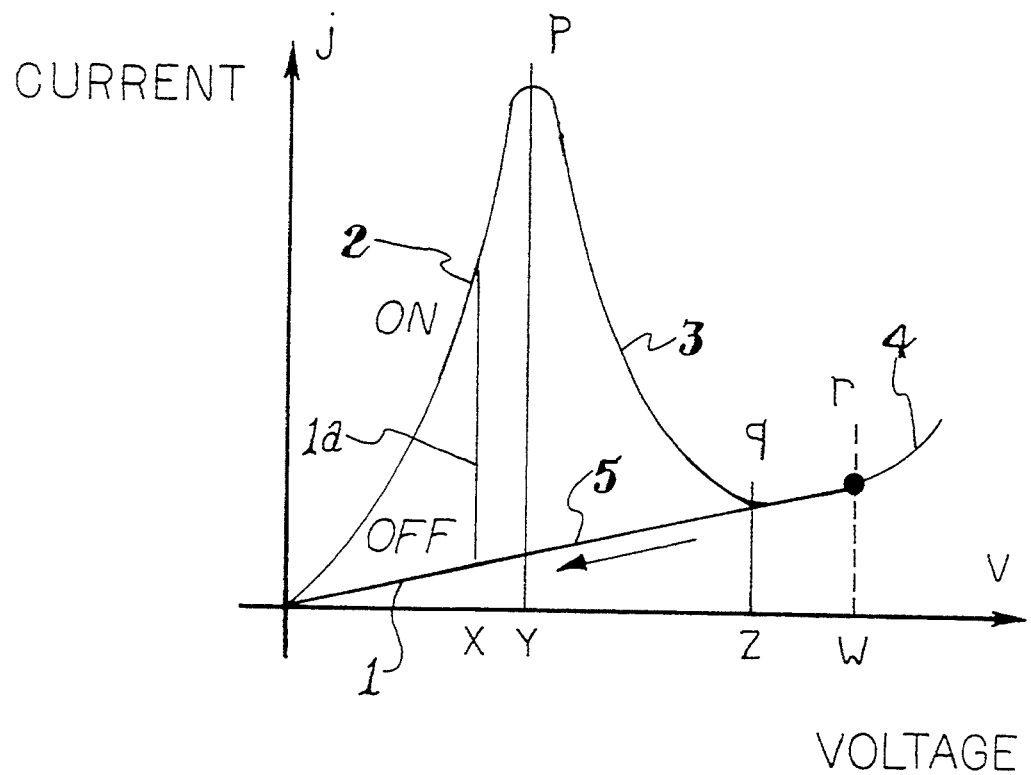
FIG. 3 is graphical representation of a portion of the jV plot of FIG. 2 in more detail.

To convert the device from the ON state to the OFF state requires that the applied voltage be removed or reduced to a value of about zero at a sufficiently high "slew rate" from a voltage above "z". As shown in FIG. 3, the jV curve of the device does not go through the current peak "p" when the applied voltage is rapidly lowered in this manner. Rather it follows a direct nearly linear path shown by line 5. Slew rates for efficiently switching the device OFF are greater than about one volt per millisecond with rates greater than about 1000 V/mS being preferred. It is to be noted that a device in the ON state may be turned OFF by a voltage pulse starting at zero, provided the pulse voltage is larger, or approximately equal to "z" wherein the pulse reaches line 4, and the fall time of the pulse meets the slew rate requirement. Typically, a voltage of ten volt for a duration of one microsecond or less is adequate.

When the device is turned OFF in the above manner, it has a high resistance, typically two or three orders of magnitude higher than its resistance in the ON state. The resistance can be determined by measuring the jV curve in the OFF state over a small range of the applied voltage up to the threshold voltage. The device will remain in the OFF state as long as the applied voltage does not exceed the threshold voltage of about three volts. In this OFF state, the thin film exhibits a high impedance as would normally be associated with an insulator. The resistivity of the device in this "OFF" state is in the range of between about $10^8$ ohm cm and about $10^{11}$ ohm cm.

When the applied voltage is raised above the threshold voltage however the thin film is rapidly converted to a state of low resistivity, and the device supports a high current density. The resistivity in this "ON" state is typically in the range of between about $10^4$ ohm cm and about $10^7$ ohm cm.

Figure 2:
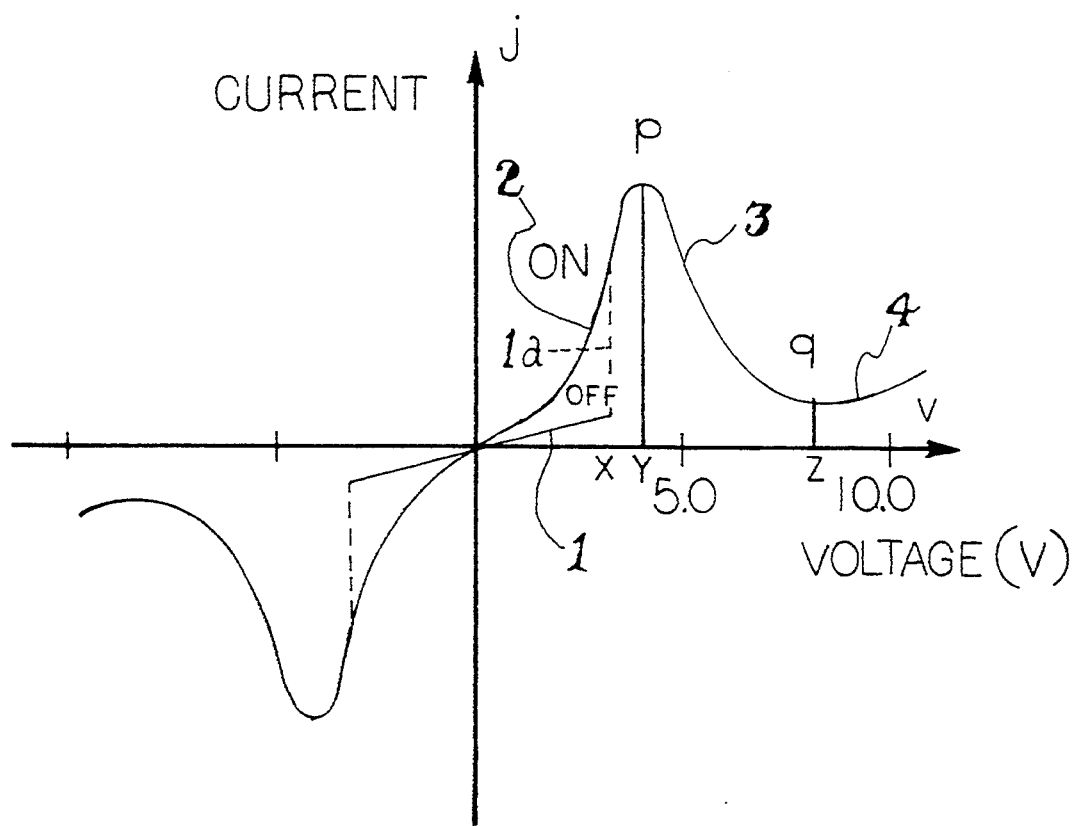
FIG. 2 is a graphical representation in the form of a jV plot of the current density versus the voltage of a device of the present invention illustrating the threshold switching behavior of the device. Current density j is defined as the current in ampere divided by the surface area of the device in square centimeters.

The threshold switching behavior is graphically displayed in FIG. 2. Line 1 shows that when the device is in the OFF state, the current density increases only slightly as the applied voltage is increased. When the applied voltage reaches the threshold voltage "x", the device rapidly switches from the OFF state to the ON state wherein the current density is suddenly increased by two or three orders of magnitude or more as shown by the dotted line. It is essential for the transition to the ON state to occur fully that the ambient of the device be free of any gaseous species from which an electron transfer to the device surface (or vice versa) can occur such as, for instance, in a chemical redox reaction. Gases for which such an electron transfer occurs when the device comes into contact with them are referred to as "reactive gases" within the scope of this invention. The sensitivity of the device characteristic to such gases constitutes the basis for using the device as a gas sensor as described below. Examples of such gaseous species are oxygen, ammonia, and nitrous oxide. The definition includes gases which become sufficiently reactive at temperatures other than room temperature, or vapors which may condense on the sensor surface below the dew point.

Once in the ON state, the jV curve follows lines 2, 3 and 4 wherein the current rises steeply with voltage in the first quadrant as shown by line 2, and symmetrically in the third quadrant, until it reaches a maximum current "p" at a voltage "y". Increasing the voltage beyond the "y" value results in a decrease in current density until a minimum "q" is reached at voltage "z". In this voltage range, the device exhibits a voltage controlled negative differential resistance or NDR as shown by line 3. Typically the values for "y" range between 4-6 V and for "z" between 8-10 V. At voltages above "z", the jV curve shows the high resistivity characteristic of an insulator which is shown as line 4.

The jV curve of the device in its ON state can be completely traced out for both increasing and decreasing voltages, through the maximum, at a sufficiently low rate of change of the applied voltage. In particular the curve is continuous through the origin which means (i) there is no holding current necessary to maintain the ON state, and (ii) the device has a "memory" of the ON state even when no voltage is applied.

According to the invention, a metal-insulator-metal (MIM) device configuration of non-dense silica is sandwiched between metal electrodes and is converted to a state in which the current through the device is sensitive to small concentrations of reactive gas in the gaseous ambient, The silica is prepared from a hydridosilsesquioxane by low-temperature pyrolysis on a substrate that functions as the bottom electrode, such as gold or nickel evaporated onto a glass substrate, a solid piece of metal, or a semiconductor. The thickness of the silica film is between 100 nm and 1.5 $\mu$m. After pyrolysis, a gold top electrode is evaporated onto the silica film. The device is brought into an inert ambient gas such as nitrogen, argon, or carbon dioxide for a sufficient time to allow the oxygen and moisture of the air to purge out. Then the device is electroformed by the application of a voltage above the forming voltage threshold of about 2-7 volt.

As a consequence of this treatment, the device exhibits a non-linear voltage-current characteristic with a current maximum. The presence of trace amounts of reactive gases such as oxygen, ammonia, and nitrous oxide in the immediate ambient of the device causes a decrease in the current which is monitored at a constant applied voltage above the reaction barrier value. This change in current can thus be used to detect these reactive gases.

After exposure to the reactive gas, the device having changed to a lower conductivity than before, can be activated again after the reactive gas has been purged out from its ambient while the voltage is reduced or removed, and by electroforming the device, as described above.

Electrical sensors can be produced for reactive gases of which oxygen, ammonia, and nitrous oxide are examples. The sensors are directly compatible with standard analog circuitry and digital signal levels and can be interfaced directly with data processing hardware and software. The sensitivity of the sensor can be adjusted by the voltage applied to the device after it is electroformed above the threshold voltage, and therefore the operating range of the sensor can be electrically adjusted. Since the sensors can be made to retain the status achieved during sensing a gas even after the gas has been removed, applications include sentinels for the transient appearance of oxidizing gases without the need for external continuous recording capability.

The thin film silica coatings derived from hydrogen silsesquioxane resin can be distinguished from the many coatings existing in the prior art by a consideration of their unique characteristics which are manifested as follows.

Initially, as a voltage below a threshold voltage "x" are applied to the device in the OFF state, the current follows an essentially linear relationship along line 1. When the threshold voltage "x" is reached however line 1a in FIGS. 2 and 3 indicates a rapid linear transition from the OFF state of the device to the ON state in which the current varies in a nonlinear fashion. As the voltage is increased beyond the threshold voltage "x", a current peak "p" is reached at voltage "y".

Once the ON characteristic of the device is established, a decrease of the voltage from "y" to zero for example, causes the current to decrease along line 2 rather than retracing lines 1a and 1. On the other hand, voltage increases beyond "y" effect a decrease of current along line 3 to the current minimum "q" at voltage "z". That part of the curve between points "p" and "q" defines the region of negative differential resistance or NDR along line 3 between the extrema. The device remains in the ON state and is free to cycle slowly along lines 2 and 3.

The device may be switched to the OFF state from a voltage approximately at or above "z", for example from "w", by rapidly reducing to a value below the threshold voltage "x", for example to zero. This causes the current to decrease to a low current in an essentially linear fashion from the return point "r" in FIG. 3 in a path along lines 5 and 1. The device remains in the OFF state as long as the magnitude of any subsequently applied voltage, either positive or negative, does not exceed the threshold voltage "x". If this voltage does exceed the threshold voltage "x", the device is switched back to the ON state as described above.

The jV curves according to FIGS. 2 and 3, therefore, can be seen to exhibit both linear and non-linear regions for a device. The jV curve has a first non-linear region 2 "ON" followed by a second non-linear region of negative differential resistance 3 "NDR", and a third region 5 which can be anterad by a rapid removal of an applied voltage "w" causing the current to decrease from point "r" in a linear fashion along lines 5 and 1 "OFF". The jV curve has a fourth region 1a at a threshold voltage "x" where a rapid transition from region 1 to region 2 occurs.

With reference again to the drawing, the gas sensor device according to the present invention is a two-terminal component which functions as a resistor in an electrical or electronic circuit. The resistance of the device, at least one surface of which is exposed to the gaseous ambient, depends on the partial pressure of a reactive gas such as oxygen, carbon monoxide, or ammonia in this ambient. The current through the device at a constant applied voltage is a measure of the concentration of the reactive gas.

The response of the device to the reactive gas depends additionally on the applied voltage. With the device in its conductive state (switched ON in an inert ambient by exceeding the threshold voltage temporarily), the exposure to a reactive gas, for instance oxygen (as in air) results in a decrease of the device current that is approximately exponential in time and which can be characterized by a time constant. This time constant is a function of the applied voltage (kept constant during the exposure) such that the current decrease happens the faster, that is, with a smaller time constant, the higher the applied voltage.

Figure 7:
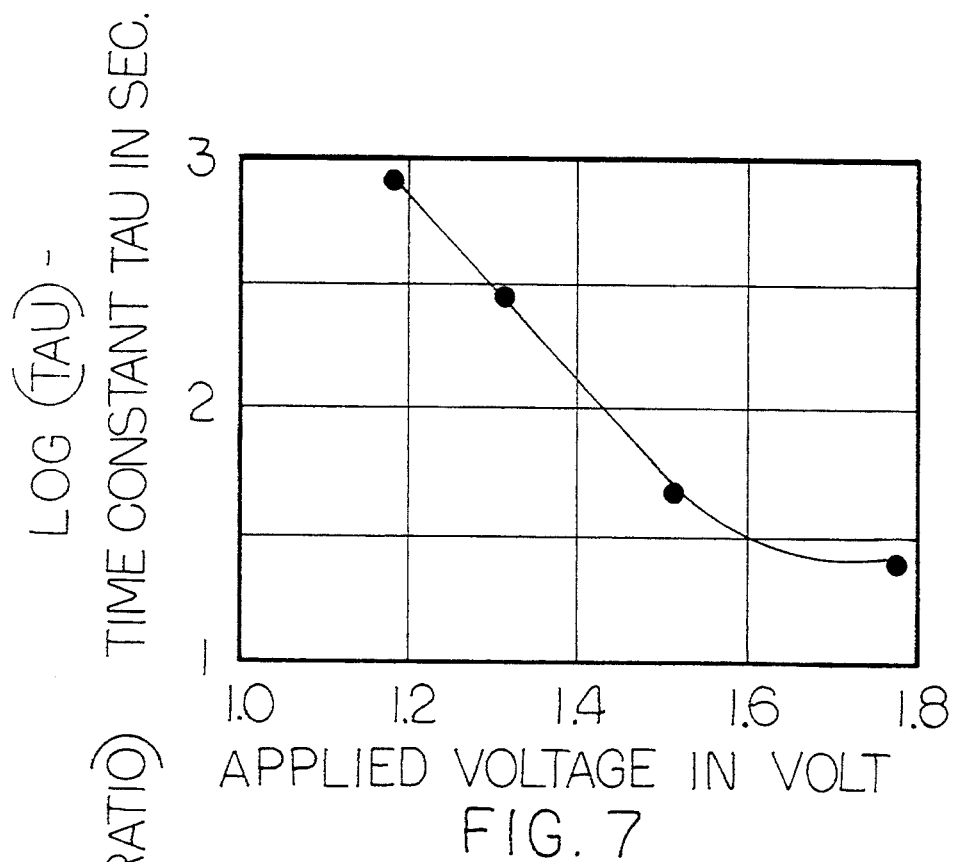
FIG. 7 is a graphical representation showing the time constant with which the current through the gas sensor decreases in response to exposure to oxygen (air) as a function of applied voltage. The time constant decreases with increasing voltage, that is, the gas sensor responds the faster the higher the voltage. Values as low as a few seconds are reached for voltages above 1.8 V.

FIG. 7 shows the dependence of the characteristic time constant on the applied voltage for a device exposed to air. At small voltages, the device response is very slow. A linear extrapolation gives a limiting voltage of $\sim 1.1$ V below which the device does not respond to the presence of the reactive gas. This limit is termed the reaction barrier voltage $V_{eb}$. It is, therefore, possible to expose a device in its conductive state to a reactive ambient without the device switching itself OFF if the applied voltage is less than $V_{eb}$.

The applied voltage, in addition to the time constant of the effect, also controls the amount by which the current decreases. The ratio of initial current to the current reached at long times after exposure to a reactive gas increases with the applied voltage.

Figure 8:
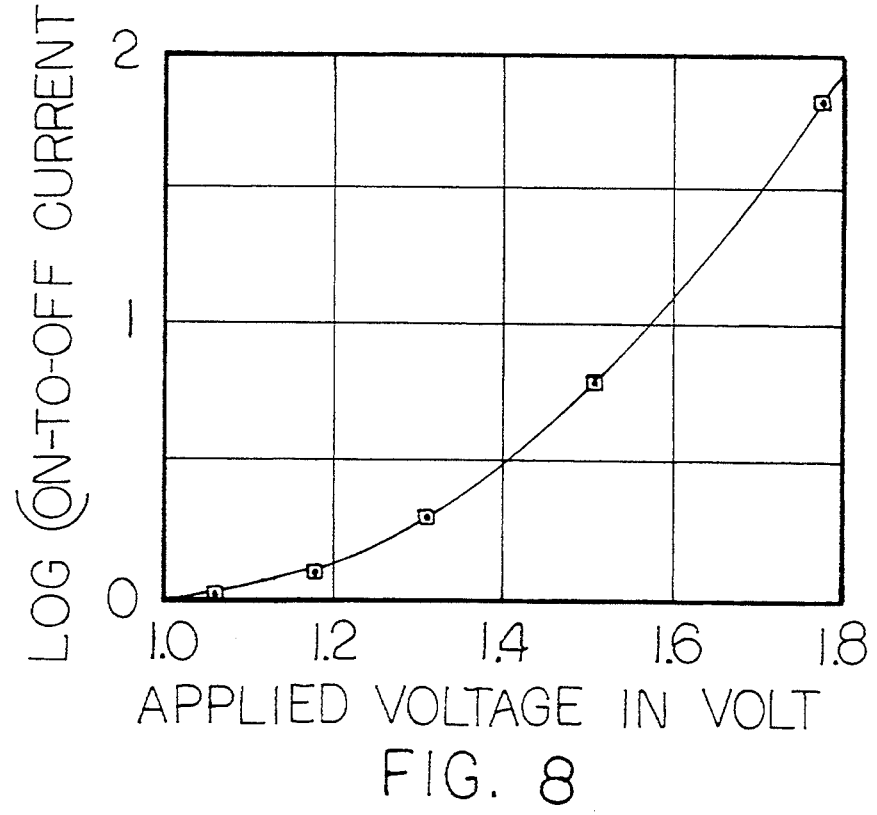
FIG. 8 is a graphical representation showing the ratio of the ON current to the OFF current of the gas sensor exposed to oxygen plotted logarithmically against the voltage applied to the gas sensor. The plot shows a quadratic dependence, and at voltages above 1.8 V the ratio exceeds a factor of one hundred.

In FIG. 8, the logarithm of the ratio is plotted against the applied voltage and shows a quadratic dependence. It is thus possible to control the response characteristics of the device when used as a sensor so that both the time constant and the dynamic range of the response can be adapted to specific sensor applications.

Figure 4:
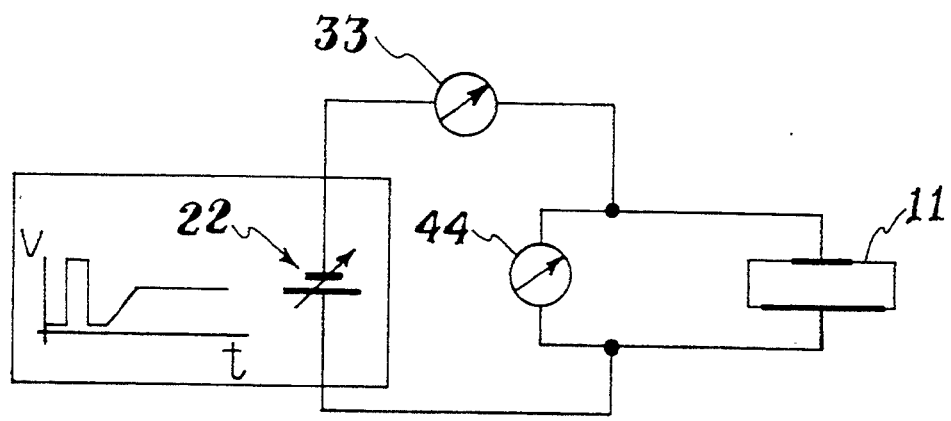
FIG. 4 is a schematic wiring diagram of a test circuit for measuring the current and the threshold voltage of the gas sensor of the present invention in a typical application of the gas sensor.

A typical application is shown in the test circuit of FIG. 4. The resistive device component 11 is connected to a variable voltage source 22 and a current meter 33 in series with it. The current meter 33 can consist of a calibrated measurement resistor and a voltmeter to measure the voltage drop across it. A voltmeter 44 connected across two terminals of the device measures the voltage applied to the component 11.

Figure 5:
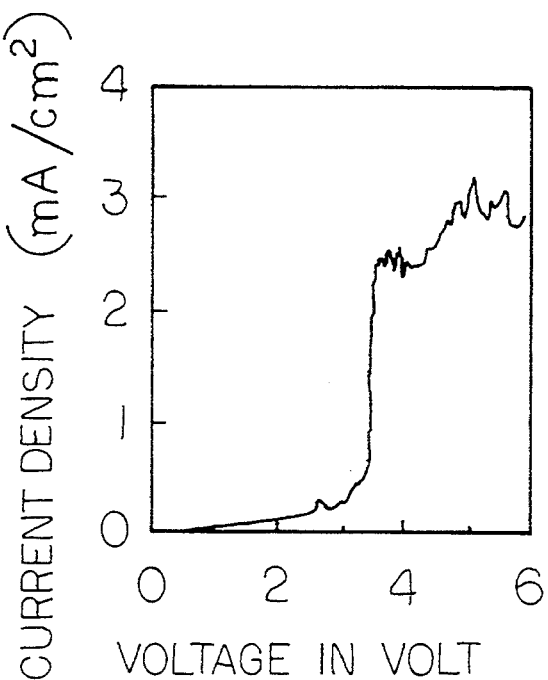
FIG. 5 is a graphical representation of a voltage current plot of the gas sensor in the OFF state showing the transition from OFF to ON at a threshold voltage having a value of 3.35 V.
Figure 10:
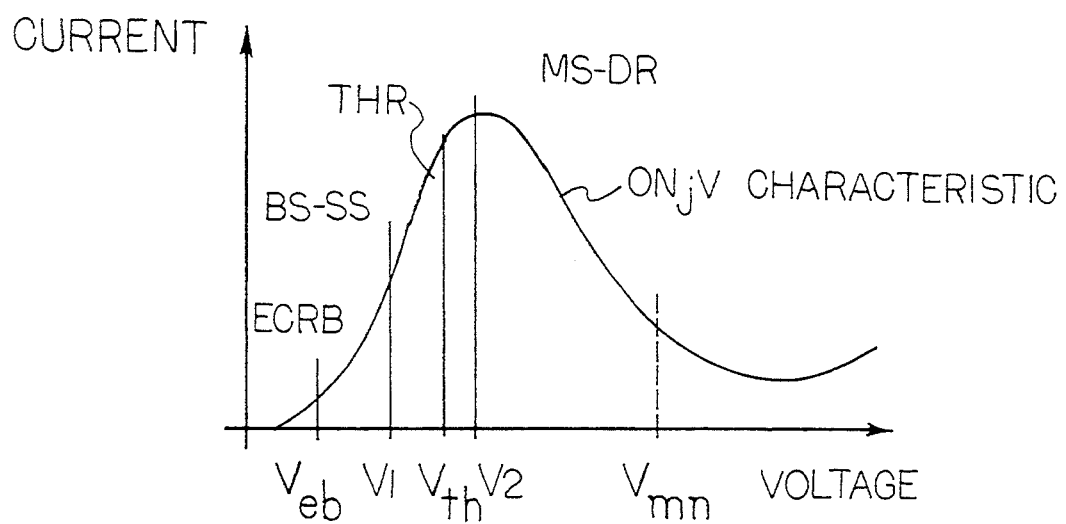
FIG. 10 is a graphical representation of a portion of the jV plot similar to FIG. 3, but showing the ON and OFF characteristics of the gas sensor of the present invention.

The two modes of operation with the resistive component connected as a gas sensor in the circuit of FIG. 4 are the determination of the threshold voltage of the device in its use as a gas monitor, and the measurement of the device current in a use of the device as a gas sentinel. The procedures for using the device in either of the two modes are described below, 1. Monitor—Threshold Determination The device is switched OFF by applying a voltage pulse to the device as described previously. The pulse voltage reaches into the valley of the jV-curve of the device as shown in FIG. 10. This is typically a voltage between 9 V and 10 V. The device is now in the OFF state. Starting at a small voltage below the reaction barrier (ECRB) $V_{eb}$, for example at 0 V, the applied voltage is slowly ramped up until the device switches from OFF to ON. The voltage at which this occurs is the threshold voltage, and it is determined from the rapid increase of current during the switching event by a factor between 3 and 100 within an interval of about 50 mV. A representative event with a threshold voltage of 3.35 V is shown in FIG. 5. The device is then pulsed OFF again and a new determination of the threshold voltage is made. This sequence is repeated for every measurement of the partial pressure of the reactive gas in the ambient.

The threshold voltage is a monotonically increasing function of the partial pressure of the reactive gas in the sensor ambient, or the concentration of the oxygen. The calibration that relates the threshold voltage to the oxygen concentration in nitrogen ambient at atmospheric pressure is shown in FIG. 6.

Figure 6:
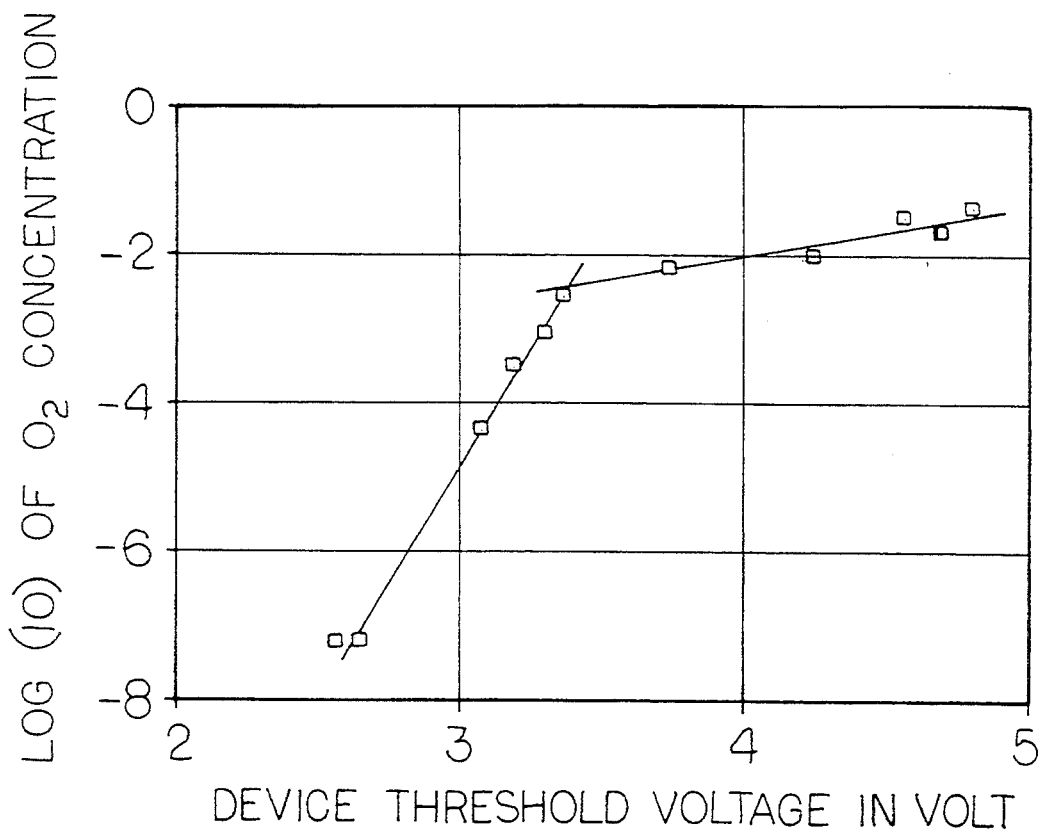
FIG. 6 is a graphical representation showing the relationship between the oxygen partial pressure at the gas sensor and the threshold voltage in a semi-logarithmic plot with the partial pressure of oxygen given as the decadic logarithm.

FIG. 6 shows that a change in the characteristic of the sensor occurs at about 0.5% oxygen concentration. It also shows the wide range and high sensitivity to oxygen which the sensor exhibits. The lower limit of 50 parts per billion (at a threshold voltage of 2.6 V) is given by the trace contamination of oxygen in the nitrogen purge gas.

2. Sentinel—Current Measurement

The device is exposed to an inert atmosphere such as nitrogen or argon for a sufficiently long time and then electro-formed to switch it into its ON position as described previously. A constant voltage above the reaction barrier $V_{eb}$ is then applied and the device current is measured continuously at this voltage. If the concentration of the reactive gas in the sensor ambient rises above the sensitivity limit, the current drops precipitously to the value given by the OFF device characteristic. In this way a single occurrence of an excessive gas concentration can be detected. The behavior of the device following its triggering to the OFF state is determined by the applied voltage and falls generally into two different regimes of operation shown in FIG. 10:

(i) Single shot fuse (analogous to a bistable flip-flop) for voltages $V_1$ below the threshold voltage $V_{th}$, i.e., $V_{eb} < V_1 < V_{th}$, and (ii) Delayed self-recovery fuse (monostable flip-flop) for voltages $V_2$ above the threshold voltage $V_{th}$, i.e., $V_{th} < V_2 < V_{mn}$ where $V_{mn}$ is the voltage of the current minimum of the ON state.

The first regime is operational when the voltage $V_1$ applied to the device is between the reaction barrier voltage $V_{eb}$ and the threshold voltage $V_{th}$. When an even momentary exposure to oxygen or other reactive gas occurs, the current drops and will stay low, and the device is switched OFF. The device will stay OFF even if the ambient atmosphere becomes completely free of the gas once more until the device is reset by switching it back ON with a voltage in excess of the threshold voltage $V_{th}$ (electro-forming in inert ambient) with the reactive gas below the sensitivity limit of the device.

The device can function as a sentinel which permanently records a single occurrence of excessive gas concentration. The sensitivity of the device, and the rate of current loss is determined by the applied voltage. The higher $V_1$ is above the reaction barrier $V_{eb}$ the more sensitive is the device. The rate of current loss is determined by the time constant of the exponential decay of the device current. The time constant is a function of the applied voltage for a given oxygen concentration; for air, this function is shown in FIG. 7.

In a similar fashion, the applied potential controls the amount of current loss and this is shown in FIG. 8 for oxygen, where the logarithm of the ratio of initial current (ON) to final current (OFF) is plotted vs. the applied voltage. Thus, at increased voltage, the device is more sensitive and responds faster and with a larger change in current than when operated at lower voltage.

The second regime is operational when the voltage $V_2$ applied to the device is above the threshold voltage $V_{th}$ but below the voltage of the current minimum $V_{mn}$. Preferably the voltage is set close to where the current maximum is reached as shown in FIG. 10. When an even momentary exposure to oxygen or other reactive gas occurs, the current drops and again the device is switched OFF. Since the applied voltage in this regime is high, the response is very fast, of the order of one second. The device will stay OFF as long as the reactive gas is present at a concentration above the sensitivity limit. It will recover once the reactive gas is removed with a time constant that depends on the applied voltage. The higher the voltage, the faster the device will recover and return to its previous ON current.

Figure 9:
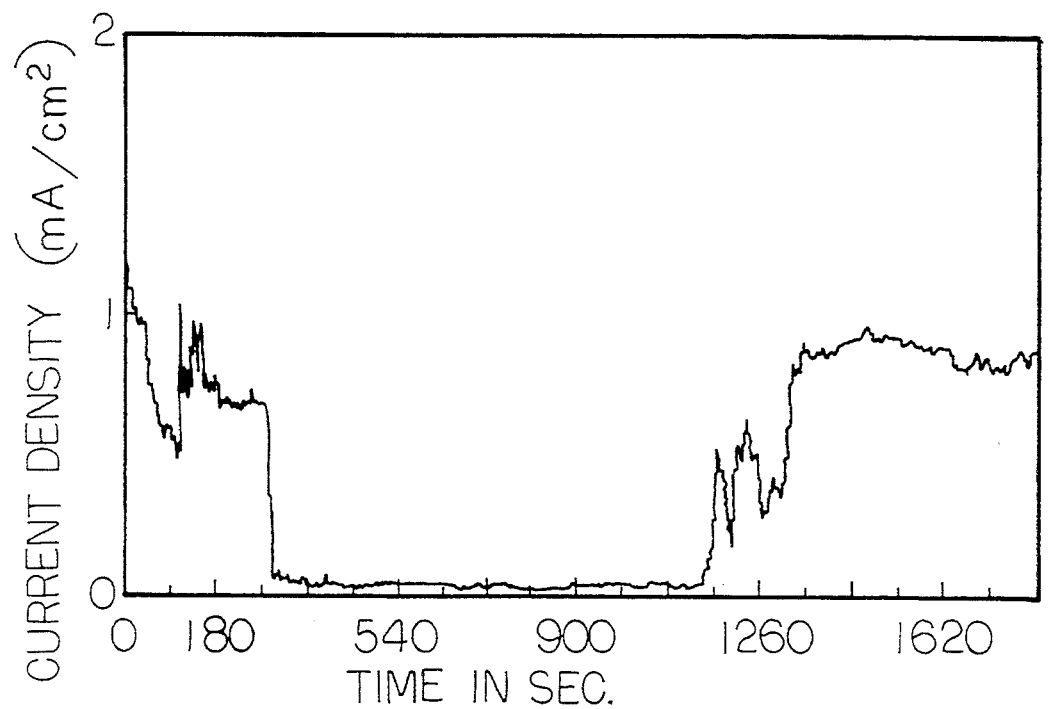
FIG. 9 is a graphical representation of the current through the gas sensor at an applied voltage of 4.2 V plotted as a function of time. This figure shows the drop in current at the admission of oxygen to the gas sensor ambient, and its recovery after removal of the oxygen by a continuing purge with nitrogen gas. The oxygen was admitted at time t=256 s. Initial oxygen concentration was 1.7% (partial pressure 17.2 mbar) with a nitrogen purge maintained at a flow rate of 1.5 l/min into a volume of 5.75 l.

FIG. 9 shows an example of this behavior. Thus, the dead time of the sentinel can be controlled by the applied voltage. A minimal dead time is given by the desorption process of the reactive gas from the device surface and bulk and depends ultimately on the gas to which the sentinel device was exposed.

Other variations and modifications may be made in the method and device described herein without departing from the essential features and concepts of the present invention. The forms of the invention described herein are exemplary only and are not intended as limitations on the scope of the invention as defined in the appended claims.

That which is claimed is:

1. A method of detecting the presence of a reactive gas in an inert ambient gas comprising (a) exposing part of a film surface to the inert ambient gas; the film being a silicon dioxide derived from the oxidation of a hydrogen silsesquioxane resin; the silicon dioxide film having a jV plot of the current density versus the voltage which includes linear and nonlinear regions, the jV plot of the film including; (i) a first nonlinear region where the current increases with the applied voltage to a maximum; followed by (ii) a second nonlinear region of negative differential resistance leading to a current minimum at and beyond which (iii) a third region is reached from where the rapid decrease of the applied voltage causes the current to decrease linearly with voltage; the jV curve of the silicon dioxide film further including (iv) a fourth region where an increase of the voltage applied to the film across a threshold value causes a rapid transition of the current from the linear region to the first non-linear region (i); the next step being selected from the group consisting of (b) measuring the change in the current flow through the film at an increasing voltage to determine a threshold voltage as a measure of the concentration of the reactive gas in the inert ambient gas, and (c) measuring the change in the current flow through the film at a constant voltage above a reaction barrier voltage as an indication of the presence of the reactive gas in the inert ambient gas.

2. A method according to claim 1 in which the film is purged in an inert atmosphere and the reactive gas is desorbed from the film prior to placing the film in the inert ambient gas; and in which the film with the reactive gas desorbed and purged is sensitized to the presence of a reactive gas by applying to the film a voltage in excess of the threshold voltage in an inert atmosphere prior to placing the film in the inert ambient gas.

3. A method according to claim 2 in which the voltage applied to the film is lowered below the threshold voltage but at a value above the reaction barrier voltage prior to exposing the film in the inert ambient gas to the reactive gas.

4. A method according to claim 3 in which the film is exposed to the reactive gas in the inert ambient gas, after which the reactive gas is purged and desorbed from the film surface; the applied voltage is temporarily increased to a value above the threshold voltage a second time in an inert atmosphere in order to re-sensitize the film; and in which the film is exposed again to the presence of a reactive gas in the inert ambient gas.

5. A method according to claim 1 in which the voltage applied to the film is cycled between a value in or above the region of negative differential resistance, and a value below the reaction barrier by rapidly decreasing the voltage, and slowly increasing the voltage in order to determine the threshold voltage at which the device changes from the fourth region to the first non-linear region, as indicated by a rapid and large increase in the current through the film.

6. A method according to claim 2 in which the reactive gas is selected from the group consisting of oxygen, ammonia and nitrous oxide.

7. A method according to claim 2 in which the inert ambient gas and the inert atmosphere are selected from the group consisting of nitrogen, argon, carbon dioxide, and helium.

8. The method of claim 1 wherein the film is formed by coating a substrate with a solution of a hydrogen silsesquioxane in a solvent, evaporating the solvent to form a coating, and pyrolyzing the coating to form the film.

9. A method of detecting the presence of a reactive gas in an inert ambient gas comprising (a) exposing to the inert ambient gas one of two electrodes of a variable resistor which are in direct contact with an oxide material of silica derived from a precursor of hydrogen silsesquioxane; the next step being selected from the group consisting of (b) measuring the change current flow through the variable resistor at an increasing voltage to determine a threshold voltage as a measure of concentration of the reactive gas in the inert ambient gas, and (c) measuring the change in current flow through the variable resistor at a constant voltage above a barrier voltage as an indication of the presence of the reactive gas in the inert ambient gas.

10. A method according to claim 9 in which the oxide material is in the form of a film; the film is purged in an inert atmosphere and the reactive gas is desorbed from the film prior to placing the film in the inert ambient gas; and in which the film with the reactive gas purged and desorbed is sensitized to the presence of a reactive gas by applying to the film a voltage in excess of the threshold voltage in an inert atmosphere prior to placing the film in the inert ambient gas.

11. A method according to claim 10 in which the voltage applied to the film is lowered below the threshold voltage but at a value above the barrier voltage prior to exposing the film in the inert ambient gas to a reactive gas.

12. A method according to claim 11 in which the film is exposed to a reactive gas in the inert ambient gas, after Which the reactive gas is purged and desorbed from the film surface; the applied voltage is temporarily increased to a value above the threshold voltage a second time in an inert atmosphere in order to re-sensitize the film; and in which the film is exposed again to the presence of a reactive gas in the inert ambient gas.

13. A method according to claim 9 in which the voltage applied to the film is cycled between a value below the barrier voltage by rapidly decreasing the voltage, and slowly increasing the voltage in order to determine the threshold voltage.

14. A method according to claim 10 in which the reactive gas is selected from the group consisting of oxygen, ammonia, and nitrous oxide.

15. A method according to claim 10 in which the inert ambient gas and the inert atmosphere are selected from the group consisting of nitrogen, argon, carbon dioxide, and helium.

16. The method of claim 10 wherein the film is formed by coating a substrate with a solution of hydrogen silsesquioxane in a solvent, evaporating the solvent to form a coating, and pyrolyzing the coating to form the film.

* * * * *